US009174006B2

(12) United States Patent
Vosseler et al.

(10) Patent No.: US 9,174,006 B2
(45) Date of Patent: Nov. 3, 2015

(54) DERMAL ACCESS DEVICE

(75) Inventors: Michael Vosseler, Bad Duerrheim (DE); Kai Hiltmann, Coburg (DE); Michael Jugl, Dauchingen (DE)

(73) Assignee: Hahn-Schickard-Gesellschaft Fur Angewandte Forschung E.V., Villingen-Schwenningen (DE)

(*) Notice: Subject to any disclaimer, the term of this patent is extended or adjusted under 35 U.S.C. 154(b) by 0 days.

(21) Appl. No.: 13/576,562

(22) PCT Filed: Feb. 1, 2011

(86) PCT No.: PCT/EP2011/051421
§ 371 (c)(1),
(2), (4) Date: Oct. 16, 2012

(87) PCT Pub. No.: WO2011/095494
PCT Pub. Date: Aug. 11, 2011

(65) Prior Publication Data
US 2013/0041318 A1    Feb. 14, 2013

(30) Foreign Application Priority Data

Feb. 2, 2010    (DE) .......................... 10 2010 001 506

(51) Int. Cl.
*A61M 5/32*  (2006.01)
*A61M 5/142*  (2006.01)
(Continued)

(52) U.S. Cl.
CPC ........... *A61M 5/3287* (2013.01); *A61M 5/3293* (2013.01); *A61M 5/46* (2013.01);
(Continued)

(58) Field of Classification Search
CPC .................... A61M 2005/1588; A61M 5/158; A61M 5/46; A61M 5/3293; A61M 2005/14252; A61M 5/3287

USPC .......................................... 604/174–180, 117
See application file for complete search history.

(56) References Cited

U.S. PATENT DOCUMENTS 4,512,768 A * 4/1985 Rangaswamy ................ 604/191
5,437,640 A    8/1995 Schwab
(Continued)

FOREIGN PATENT DOCUMENTS

AU    8704582 A    9/1983
CN    101557845 A    10/2009
(Continued)

OTHER PUBLICATIONS

International Search Report and Written Opinion of the International Searching Authority for PCT/EP2011/051421 mailed Jun. 6, 2011 (9 pages).

*Primary Examiner* — Theodore Stigell
*Assistant Examiner* — Benjamin Koo
(74) *Attorney, Agent, or Firm* — Harris Beach PLLC

(57) ABSTRACT

A dermal access device for fluid injection comprising a bearing block for fixation of the device onto a patient's skin, a slider movably connected to the bearing block and a hollow needle arranged at the slider for puncturing the skin, wherein the needle creates a puncture angle with respect to the skin surface when puncturing the skin, which does not exceed 25°. A dermal access device for fluid injection comprising a bearing block for fixation of the device onto a patient's skin, a movable slider connected to the bearing block and a hollow needle arranged at the slider for puncturing the skin, wherein the device comprises a first stop for limiting a first moving direction of the slider at a first puncture position of the needle, where the device comprises a second stop at a second puncture position of the needle for limiting the second moving direction of the slider.

11 Claims, 5 Drawing Sheets

(51) Int. Cl.
   *A61M 5/158* (2006.01)
   *A61M 5/46* (2006.01)
   *A61M 5/20* (2006.01)

(52) U.S. Cl.
   CPC ....... *A61M 5/20* (2013.01); *A61M 2005/14252* (2013.01); *A61M 2005/1585* (2013.01); *A61M 2005/1586* (2013.01); *A61M 2005/1587* (2013.01); *A61M 2005/1588* (2013.01)

(56) References Cited

U.S. PATENT DOCUMENTS

| | | | |
|---|---|---|---|
| 6,994,691 | B2 | 2/2006 | Ejlersen |
| 8,083,715 | B2 | 12/2011 | Sonoda et al. |
| 2002/0077599 | A1 | 6/2002 | Wojcik |
| 2004/0147901 | A1 | 7/2004 | Py et al. |
| 2004/0247902 | A1 | 12/2004 | Chuang |
| 2007/0191780 | A1 | 8/2007 | Modi |
| 2008/0154205 | A1 | 6/2008 | Wojcik |
| 2008/0269687 | A1 | 10/2008 | Chong et al. |
| 2009/0069750 | A1* | 3/2009 | Schraga .................. 604/167.02 |
| 2012/0136300 | A1* | 5/2012 | Schoonmaker et al. ...... 604/117 |

FOREIGN PATENT DOCUMENTS

| | | | |
|---|---|---|---|
| DE | 1055760 | B | 4/1959 |
| GB | 2436526 | A | 10/2007 |
| JP | 1989-068052 | | 5/1989 |
| JP | 1994-013850 | | 2/1994 |
| JP | 2005518253 | A | 6/2005 |
| JP | 2007111537 | A | 5/2007 |
| JP | 2007143635 | A | 6/2007 |
| WO | WO-9507722 | A1 | 3/1995 |
| WO | WO-02100457 | A2 | 12/2002 |
| WO | WO-03088835 | A2 | 10/2003 |
| WO | WO-2007052662 | A1 | 5/2007 |
| WO | WO-2009024521 | A2 | 2/2009 |
| WO | WO 2011/034516 | * | 3/2011 .............. A61M 5/00 |

* cited by examiner

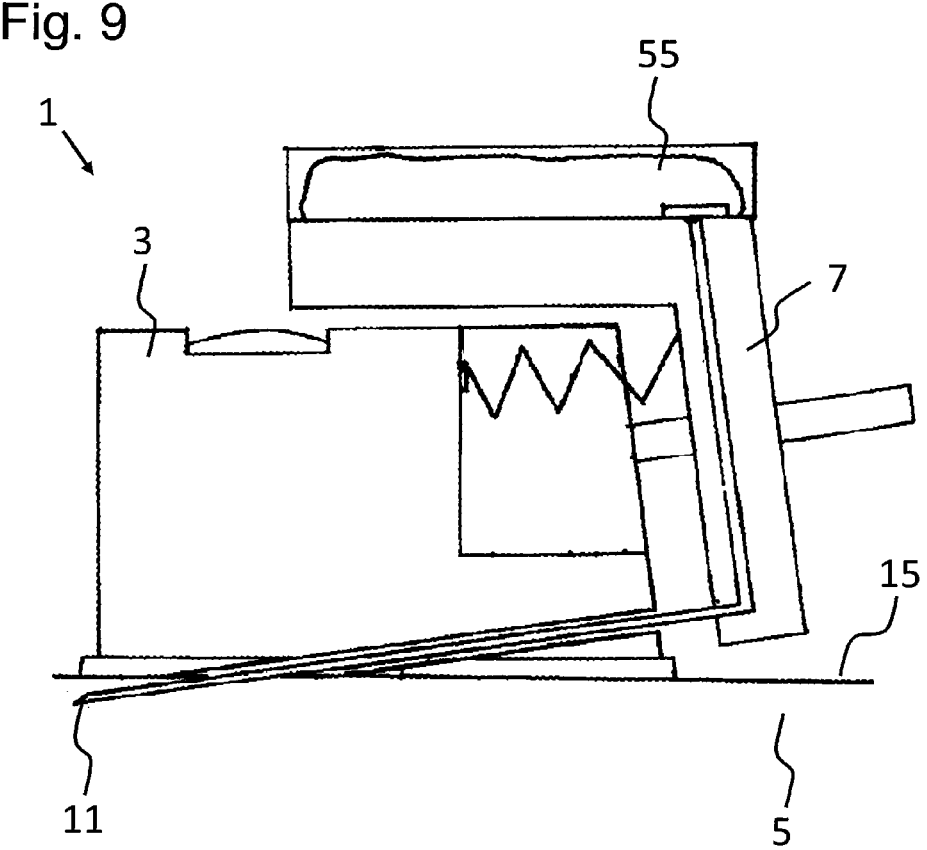

DERMAL ACCESS DEVICE

CROSS-REFERENCE TO RELATED APPLICATIONS

This application is a national stage application under 35 U.S.C. §371 of PCT Application No. PCT/EP2011/051421, entitled "Dermal Access Device," filed Feb. 1, 2011, which claims priority to and the benefit of German Application No. 102010001506.7, filed Feb. 2, 2010, which is incorporated herein by reference in its entirety.

FIELD OF THE INVENTION

The present invention concerns a dermal access device for fluid injection with a bearing block for fixation of the dermal access device onto the skin of a patient, a slider movably connected to the bearing block and a hollow needle arranged at the slider for puncturing the skin.

The present invention further concerns a dermal access device for fluid injection with a bearing block for fixation of the dermal access device onto the skin of a patient, a movable slider connected to the bearing block and a hollow needle arranged at the slider for puncturing the skin, wherein the dermal access device is provided with a first stop for limiting a first moving direction of the slider at a first puncture position of the hollow needle.

BACKGROUND OF THE INVENTION

From the US-document U.S. Pat. No. 7,556,615 B2, for example, a microneedle access device is known, which is provided with a protruding ring-shaped skin pre-stressing device. This skin pre-stressing device encloses the microneedle, and it touches the skin surface of the patient before puncturing the skin, shortly after the microneedle deformed the skin through contact. With the ring-shaped skin pre-stressing device, the deformation of the skin surface is minimized, which allows for a more precise penetration of the microneedle.

Further, from the international patent application publication WO 2007/061972 A2 an access device for injectable substances is known, that is provided with a hollow needle of sufficient length in order to penetrate into the skin of a patient. The access device is provided with a delimiter for controlling the penetration depth of the hollow needle as well as a stabilizer that is positioned at a distance to the delimiter. Deformation of the tissue close to the puncture position is avoided with the stabilizer, so that the depth where the substance is introduced is essentially determined through the length of the hollow needle.

The US-document US 2004/0147901 A1 discloses an intradermal application device, provided with a vacuum chamber in order to achieve an essentially flat puncture area for the hollow needle on the skin. The angle between the axis of the device and the skin is 45° in one embodiment, but can be every angle between 30° and 60° in other embodiments.

Further, from an international patent application publication WO 2009/086463 A1 a device for applying a substance is known, which is provided with a sealed package with a squeezable reservoir, containing the substance. Further, a hollow needle is envisioned for the application of the substance, which is a therapeutic liquid.

Problem to be Solved by the Invention

The underlying problem of the invention is to provide a dermal access device that is improved compared to the state of the art. Particularly, the dermal access device shall provide a reliable and precise intradermal injection. Further, the injection with the dermal access device should be comfortable for the patient.

Solution According to the Invention

The reference numbers in all claims have no limiting effect but only serve the purpose of improving readability.

For solving the problem, the invention teaches a dermal access device with the features of claim 1. A dermal access device for fluid injection is to be understood as an apparatus for injecting a liquid for medical purposes by means of a hollow needle that punctures the skin of a patient. In connection with the invention, the term injection of a liquid also comprises medical infusions of the liquid. With the help of an injection, active pharmaceutical ingredients, in particular medicaments, can be administered to the patient. For puncturing the skin of a patient, a hollow needle is usually provided with a needle tip. In the present invention, the needle tip is the end of the hollow needle which is facing away from the slider. Via an opening in the needle tip, the liquid can exit the needle during injection and is injected into the tissue. In order to facilitate the skin puncturing further, known hollow needles are cut at an angle at the tip. Due to the angled cut the hollow needle has a sharp angle at the needle tip, and the needle tip opening opens at a certain reach along the hollow needle. The cut's angle usually measures 15°. During the injection or infusion, the liquid can be passed from a fluid reservoir through the hollow needle to the needle's tip in order to be injected into the tissue of the patient.

Because the slider is movably connected to the bearing block, the movement of the slider relative to the bearing block can, advantageously, also move the hollow needle arranged at the slider relatively to the bearing block. By using the dermal access device as intended, the bearing block is fixed on the skin of a patient such that the slider will be moved relatively to the bearing block during an actuation and the hollow needle will punctuate the skin.

Because the hollow needle has a puncture angle which is not exceeding 25° with respect to the skin surface when puncturing the skin, it is achievable, that the dermal access device punctuates the skin at a puncture angle that also a doctor would choose, if e.g. he punctuates the skin with a hollow needle for an intradermal injection. Advantageously, the part of the skin above the subcutis can be reached reliably with the punctuation angle according to the invention, so that a reliable and precise intradermal injection is possible. An intradermal injection, in the sense of this invention is an injection in the part of the skin which is above the subcutis. Typically, the boundary between dermis (the skin layer above the subcutis) and the subcutis is situated in a depth of 1.5 to 2.5 mm; see e.g. Laurent A. et al., "Echographic measurement of skin thickness in adults by high frequency ultrasound to assess the appropriate microneedle length for intradermal delivery of vaccines", Vaccine, 2007, Vol. 25, Issue 34, pp. 6423-6430.

For an intradermal injection via mechanical systems where the hollow needle normally punctures the skin at an angle of over 30°, when using the standard hollow needles, the difficulty arises that the liquid is leaking laterally at the puncture position as a result of a too shallow puncture depth of the needle tip and the lateral dimensions of the needle tip opening. This is usually solved by the usage of especially thin hollow needles, where the lateral dimensions of the needle tip opening are smaller than the puncture depth of the hollow needle. In contrary to that, advantageously, the puncture angle according to the invention is enabling an intradermal injection with a standard hollow needle that is e.g. available with a diameter of 0.3 mm. Then, because of the angle according to the invention, the length of the puncturing channel is large enough for the punctured skin to seal the puncturing hollow needle sufficiently from the puncture position to the needle tip opening. According to the invention, it can be exploited that the standard hollow needles are easier to fabricate or to purchase than specialized needles. Further, standard hollow needles can have a high stability, which can facilitate the handling of the hollow needle and/or the dermal access device.

Advantageously, the usage of the dermal access device is not restricted to the application of an intradermal injection, but can, in an appropriate embodiment, be utilized also for other types of injections as e.g. for a subcutaneous or an intramuscular injection, or an injection into the "junctional layer" as it is known to the person skilled in the art from e.g. WO2004/098676A2. The respective contents of WO2004/098676A2 are part of the present disclosure by reference. The type of injection to be administered can, for example, be determined through the hollow needle length in order to be able to reach the designated tissue (e.g. epidermis, derma, subcutis). Advantageously, the desired type of injection can be realized through a purely mechanical system.

Further, the invention for solving the problem teaches a dermal access device with the features of claim 2. A stop in the sense of the present invention is a means for limiting in the designated use of the dermal access device the movement of the slider in at least one moving direction. In the first and second puncture position of the hollow needle according to the invention, the hollow needle is located at least partly inside the skin of the patient. In other words, the hollow needle tip is positioned in the first and second puncture position in such a way that the skin surface is located in between the needle tip and the dermal access device. Because of the fact that the slider is limited through the first stop at the first puncture position of the hollow needle in the first moving direction, advantageously, a further movement of the slider in the first moving direction can be prevented. In the first moving direction, the hollow needle can for example puncture the skin, where the maximum puncture depth into the skin is determined through the first stop. In other words, the hollow needle tip has the maximum puncture depth into the skin at the first puncture position.

It is an achievable advantage of the second stop according to the invention that the bulge formed in the process of skin puncturing can be relaxed again in order to allow for a comfortable injection for the patient. By means of the second stop it is achievable that the hollow needle can be retracted a little towards the second moving direction after puncturing the skin with the hollow needle, which can relax the skin again. In other words, the dermal access device according to the invention permits at first during puncturing with the hollow needle the formation of a bulge, but afterwards this can, advantageously, be reduced or even completely removed through partial reversion of the puncturing process. Thus, a comfortable injection for the patient at the puncture position with relaxed skin can be achieved when the hollow needle is located at the second puncture position.

Preferred Embodiment of the Invention

Advantageous embodiments and improvements, which can be utilized individually or in combination with each other, are subject of the dependent claims.

In a preferred embodiment of the invention, the hollow needle constitutes a puncture angle with the skin surface that does not exceed 25° when puncturing the skin, wherein the puncture angle more preferably matches the angle that the hollow needle constitutes with the skin surface in the first and/or second puncture position. More preferable, the puncture angle does not exceed 20°, more preferably not 15°. More preferable, the puncture angle measures between 5° and 15°. More preferably the puncture angle is approximately 10°, which can especially be suited for an intradermal injection. Advantageously, because of the puncture angle according to the invention, the hollow needle can be applied at such a puncture angle via the movement of the slider towards the first moving direction, which also a doctor would use for application of an intradermal injection. More preferably, the hollow needle tip is situated less than 1.5 mm beneath the skin surface during the injection, more preferable 1 mm or less. More preferably, the needle tip is situated more than 0.1 mm beneath the skin surface during the injection, more preferably 0.35 mm or more. Typically, the needle tip is situated approximately 0.5 mm beneath the skin surface. More preferably, the hollow needle is situated in the second puncture position during the injection. Further, with a puncture angle according to the invention, a long puncture channel can be obtained, so that a very good sealing of the hollow needle through the skin can be achieved. In this way, a leakage of the liquid through the puncture channel can be avoided during the injection.

A preferred stop is a mechanical stop. An elastic element for example (such as a rubber buffer or a spring) would also be possible as a stop, the elastic element preferably being positioned on the one side at the slider and on the other side at a part of the dermal access device or on the skin; more preferably for this purpose the elastic element is fixed on the slider and/or on the other a part of the dermal access device or on the skin or is being fabricated in on-piece with the slider or the other part. Such an elastic element could limit the movement of the slider, for example, via its preferred elongation (i.e. its elongation in the equilibrium state, when no external forces are acting on the elastic element) in order to provide the second stop. Also, such an elastic element could limit the movement of the slider, for example, via its maximum compression (when a spring cannot be compressed further, because all turns of the spring lie on top of each other or a protrusion has reached its maximum depth compressed in the rubber buffer) in order to provide the first stop.

More preferably, by reaching the first stop, the slider is movable in other directions that are different from the first moving direction, more preferably in the second moving direction. In order to apply an injection, the hollow needle can be brought first in the first and then in the second puncture position, wherein the first puncture position differs from the second puncture position by the positioning of the slider relative to the bearing block. In a further more preferred embodiment of the invention, by reaching the second stop, the slider is movable in other directions that are different to the second moving direction, more preferably in the first moving direction.

In a further embodiment of the invention, at least two hollow needles are arranged at the slider. This way it is achievable, that the liquid is not injected punctually but is distributed over an area. Advantageously, this area can be determined by the hollow needles arranged at the slider.

In an embodiment of the invention, the slider position is fixable relatively to the bearing block in the second puncture position of the hollow needle. More preferably, the slider position is detachably fixable relatively to the bearing block in the second puncture position of the hollow needle. More preferably, the slider position is detachably fixable by means of a lock mechanism relatively to the bearing block. In this way, it is achievable that the hollow needle is not movable in the skin in the second puncture position, the more so as the dermal access device according to the invention is fixed on the patient's skin. This can allow for a more comfortable injection for the patient. Further, through the fixation of the slider in the second puncture position of the hollow needle, it can be avoided that the hollow needle is pulled out of the skin accidentally. Advantageously, the fixation of the hollow needle in the second position is detachable, so that the hollow needle can be removed from the skin after applying the injection.

According to the invention, it is envisioned, that the hollow needle is provided with a needle tip, and that the needle tip has a greater distance to the bearing block in the first puncture position than in the second puncture position. More preferably, the needle tip in the first puncture position has a first distance to the bearing block and in the second puncture position a second distance. More preferably, the first distance is greater than the second distance. Advantageously, this allows for an injection spot near the skin surface to enable an intradermal injection. Here, the injection spot is the location, where the needle tip is located inside the skin during the injection.

In a preferred embodiment of the invention, the dermal access device is provided with a guidance device for the movable connection of slider and bearing block. Advantageously, the guidance device can determine how the slider is moving relative to the bearing block, and how the hollow needle will puncture the skin. In other words, the guidance device can define the trajectory which the hollow needle follows during movement of the slider. With the help of the guidance device, the puncture angle of the hollow needle and the patients' skin can also be determined. More preferably, the guidance device is provided with at least one guiding shaft, more preferable with at least two guiding shafts. More preferably, at least one guiding shaft is arranged at the bearing block. More preferably, the slider is provided with at least one loose bearing that corresponds with the guiding shaft of the guiding device. More preferably, the number of loose bearings arranged at the slider equals the number of guiding shafts at the guiding device. Advantageously, with the help of the guiding shaft, a linear movement of the slider and the hollow needle relative to the bearing block or respectively to the patient's skin is possible. Of course, the invention also comprises embodiments, where at least one guiding shaft is arranged at the slider and at least one loose bearing is arranged at the bearing block. The invention also comprises embodiments, where at least one guiding shaft is arranged at the slider and at least one guiding shaft is arranged at the bearing block, and according to the guiding shafts, sliders and bearing blocks are provided with loose bearings correspondingly.

In a further preferred embodiment, the dermal access device is provided with a readjusting device, by which the hollow needle can be repositioned from the first to the second puncture position. More preferably, the readjusting device is provided by an elastic element. The elastic element can provide one or more stops at the same time. The elastic element can be for example a rubber buffer or a spring.

Advantageously, the hollow needle is automatically, without any interaction of the user, brought to the second puncture position via the readjusting device, when it reaches the first puncture position. More preferably, only when reaching the first puncture position, the readjusting device can reposition the hollow needle from the first to the second puncture position. More preferably, the readjusting device is arranged at the bearing block and acts on the slider. Because the readjusting device is acting on the slider, force effects on the hollow needle, which is in general more sensitive mechanically, are diminished. The rubber buffer is preferably composed of an elastic material, more preferably a thermoplastic elastomer. It is possible to fabricate the rubber buffer and the bearing block in one piece, e.g. by means of a two component injection moulding. In a more preferred embodiment of the invention, the slider is provided with one or more protrusions, e.g. realized through one or more knobs. The protrusion or the protrusions are pressed inside the rubber buffer, when the slider is brought into the first position. Preferably, the rubber buffer is pushing out the protrusions during a following disengagement in order to bring the slider to the second puncture position.

In an embodiment of the invention, the bearing block and the slider are individual parts. There are also possible embodiments of the inventions, where bearing block and slider are produced in one piece, e.g. by means of injection moulding; in this respect, it is only important that the bearing block component and the slider component of the piece can be moved relatively to each other, which is e.g. achievable, if bearing block and slider are connected via at least one flexure hinge, so that bearing block, slider and flexure hinge are one component. Also, in an advantageous embodiment of the invention, lock and detach mechanisms, e.g. lock nose and lock tongue, can be provided in one piece with their assigned components, in particular the bearing block and respectively the slider, where appropriate with one or more flexure hinges. Thus, it is advantageously achievable, that the system of bearing block, slider, lock and detach mechanisms can be fabricated in a few injection moulding steps or only in one injection moulding process.

Preferably, it is envisioned according to the invention that the hollow needle can be positioned in a resting position, and that the hollow needle is arranged within a corresponding needle guidance device of the bearing block in the resting position. More preferably, the hollow needle is stored in the dermal access device in the resting position. Advantageously, the hollow needle can be protected from mechanical influences in the resting position by the needle guidance device. Further, because the hollow needle is arranged inside the needle guidance device, the risk of injuries during usage of the dermal access device, due to a protruding needle tip, can be avoided. Further, it is achievable, that the bearing block can be first seated on the skin without having the hollow needle already puncturing the skin. Advantageously, by actuating the dermal access device, the hollow needle can exit the needle guidance device and can be punctured into the skin. More preferably, the hollow needle is exiting the bearing block on the lower surface that is fixed on the patients' skin.

More preferably, the hollow needle is situated at least partly inside the slider. Inside the slider a fluid channel can be created, through which the liquid can be transported from a fluid reservoir to the hollow needle and through the needle to the needle tip in order to be injected there. More preferably, the hollow needle protrudes a certain distance into the slider, where the fluid channel connects to. The path of the liquid in the slider preferably has a bent or buckled shape, which allows for a space saving dermal access device. For example, the channel inside the slider can be attached to the end of the hollow needle at an angle.

To further improve the invention, it is preferably envisioned that the dermal access device is provided by a fixation device, by which the bearing block is fixed onto the skin surface. More preferably, the bearing block can be fixed via the fixation device with the lower surface onto the skin surface. With the fixation device, it is achievable that unwanted forces on the dermal access device from all directions can be picked up and are passed to the skin. Further, with a suitable fixation device, the bulging of the skin can be reduced during puncturing with the hollow needle into the skin. A fixation device according to the invention can e.g. be provided by double sided tape and/or a fixation band-aid. The fixation device can also have wings that are arranged at the sides of the bearing block. The wings could e.g. be fixed with a fixation band-aid onto the skin. A further example of a possible fixation device could also be a band, similar to the band of a wrist watch, bound around the corresponding part of the body. Of course, combinations of the discussed examples are possible.

In a further preferred embodiment, an inspection device is arranged at the bearing block for viewing the puncture position of the hollow needle. More preferably, the inspection device is situated on the top side of the bearing block. More preferably, the inspection device is provided with a lens. More preferably, cross lines are arranged on the lens. Advantageously, with the inspection device, a selection and/or a precise determination of the puncture position is possible. The dermal access device can, advantageously, be positioned according to the skin structures, so that an optimal puncture position is achievable. Apart from the choice of the optimal puncture position, the puncture position can be observed during the injection process, in order to take appropriate actions in the case of complications.

To further improve the invention, it is preferably envisioned that a connection device is arranged at the slider, in order to combine the hollow needle and with a fluid reservoir. The connection device can also be described as fluidic connection. More preferably, the connection device is situated at the end of the hollow needle which is facing away from the needle tip. More preferably, the connection device is arranged at that side of the slider which is facing away from the skin surface. The connection device can e.g. be an even area where a fluid reservoir can be bonded to. Further possible embodiments of the connection device can be a luer-lock connector, a simple cone or a tube clip. There are possible other embodiments, that have connection devices, which connect the hollow needle tightly with a tubing, that leads to a fluid reservoir.

In a preferred embodiment of the invention, the connection device is provided with a filter. By using a filter, it can be avoided that dirt particles clog the hollow needle or even get injected into the skin.

According to the invention it is preferably envisioned, that the dermal access device is provided with a fluid reservoir for storing the fluid to be injected. In this way, a complete injection system can be provided. More preferably, the fluid reservoir is provided as a bag. More preferably, the fluid reservoir is connected to the slider. More preferably, the fluid reservoir is connected inseparablely to the slider.

BRIEF DESCRIPTION OF THE DRAWINGS

Further advantageous embodiments will be described in detail in the following with the help of drawings containing three exemplary embodiments, which the invention is not limited to.

Schematically it is shown in.

DETAILED DESCRIPTION WITH THE HELP OF THREE EXAMPLES OF EMBODIMENTS

In the following description of three preferred embodiments of the present invention, the same reference numbers denote the same or comparable components.

Figure 1:
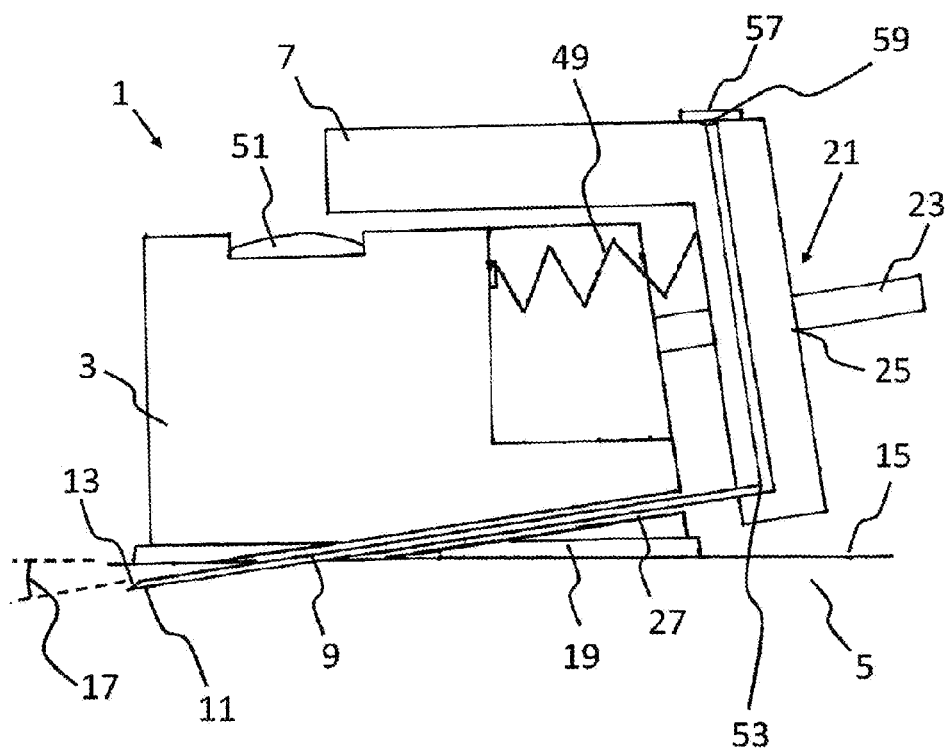
FIG. 1 a dermal access device in a sectional view.

The exemplary embodiment will be explained in the following with the help of FIGS. 1-6. In FIG. 1 a dermal access device 1 for fluid injection with a bearing block 3 for fixation of the dermal access device 1 onto the skin 5 of a patient and a slider 7 movably connected to the bearing block 3 are shown. A hollow needle 9 for puncturing the skin 5 is arranged at the slider 7, the needle being situated at least partly inside the slider 7. The hollow needle 9 is provided with a needle tip 11, which is provided with an angled cut 13 for an improved puncturing of the skin 5. The angled cut measures 15°. The needle tip 11 is the end of the hollow needle 9 which is facing away from the slider 7. Through the opening at the needle tip 11, the liquid can be injected into the skin 5. Because the hollow needle 9 is arranged at the slider 7, the slider 7 is movably connected to the bearing block 3 and the bearing block 3 is fixed in the patient's skin 5, the hollow needle 9 is puncturing the skin surface 15 when the slider 7 is moved in the first moving direction 35. When puncturing the skin 5, the hollow needle 9 and the skin surface 15 are creating a puncture angle 17, which measures approximately 10° and thus not exceeds 25°. By using this small puncture angle 17, in particular, the skin layers above the subcutis can reliably be reached in order to be able to inject the fluid to be applied intradermally.

The dermal access device 1 is provided further with a fixation device 19, with which the bearing block 3 is fixable on the skin surface 15. The bearing block 3 is fixed on the skin surface 15 with its bottom side via the fixation device 19, so that the hollow needle 9 can safely puncture the skin 5 when the slider 7 is actuated. Further, unwanted forces acting on the dermal access device 1 from all directions are picked up by the fixation device 19 and are passed on to the skin 5.

Further, the dermal access device 1 is provided with a guidance device 21 for movably connecting slider 7 and bearing block 3. Here, the guidance device 21 is provided with two guiding shafts 23 that are arranged on the bearing block. For reasons of visualisation only one of these guiding shafts is shown in FIG. 1. The slider 7 is provided with two loose bearings 25 implemented as cylindrical boreholes, which each correspond to one guiding shaft 23 of the guiding device 25. The guiding shafts 23 can slide through the loose bearings 25, which allows for a linear movement of the slider 7 relatively to the bearing block 3. Further, the puncture angle 17 of the hollow needle 9 into the skin 5 is determined by the guidance device 21.

Figure 2:
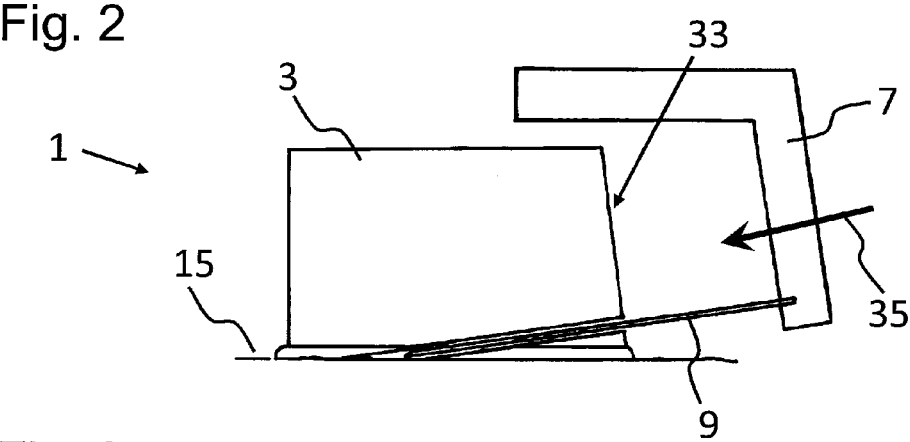
FIG. 2 a dermal access device with a hollow needle in resting position.

FIG. 2 shows a dermal access device 1 with a hollow needle 9 in the resting position, where the hollow needle 9 is arranged in a corresponding needle guidance device 27 of the bearing block 3. The hollow needle 9 is protected inside the needle guidance device 27 of the bearing block 3 when situated in the resting position. In particular, the needle tip 11 does not protrude from the bearing block 3. Thus, the danger of injury during handling the dermal access device 1 can be avoided. Further, during seating of the bearing block 3 onto the skin 5, an unwanted puncturing by the hollow needle 9 can be prevented.

Figure 3:
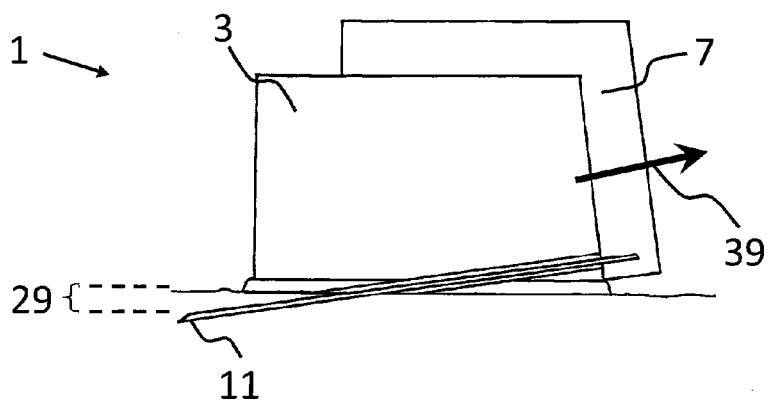
FIG. 3 a dermal access device with a hollow needle in a first puncture position.
Figure 4:
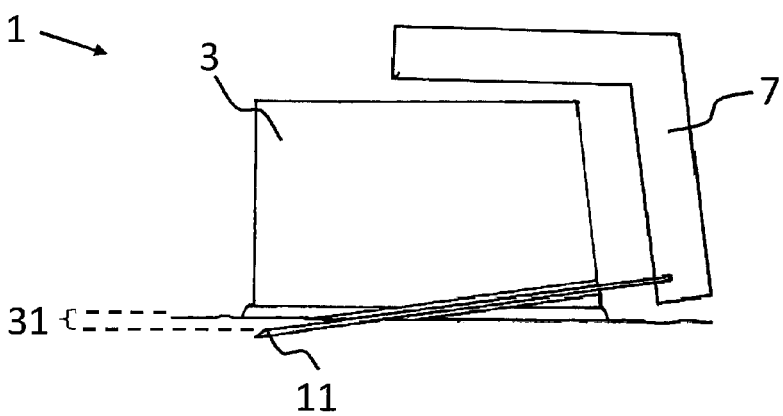
FIG. 4 a dermal access device with a hollow needle in a second puncture position.

FIG. 3 shows a dermal access device 1 with a hollow needle 9 in a first puncture position. In FIG. 4 a dermal access device 1 with a hollow needle 9 in a second puncture position is shown. As evident from FIGS. 3 and 4, the needle tip 11 is situated in the first and second puncture position inside the skin 5 of the patient, when applying the dermal access device 1 as intended. The first puncture position differs from the second puncture position by the positioning of the slider 7 relative to the bearing block 3. In the first puncture position, the needle tip 11 is distanced in a first distance 29 from the part of the dermal access device 1 that touches the skin (i.e. the bottom side of the fixation device 19). In the second puncture position, the needle tip 11 is distanced in a second distance 31 from the part of the dermal access device 1 that touches the skin, which measures 0.5 mm. In the second puncture position of the hollow needle 9, an intradermal injection can be given to the patient. As evident from FIGS. 3 and 4, the first distance 29 is greater than the second distance 31, so that the needle tip 11 in the first puncture position has a greater distance to the bearing block 3 than in the second puncture position.

The dermal access device 1 is provided with a stop 33 implemented as a mechanical stop for the limitation of the first moving direction 35 of the slider 7 at the first puncture position of the hollow needle 9. Here, the first moving direction 35 is the direction towards which the slider 7 needs to be pushed in order to bring the hollow needle 9 from the resting position into the first puncture position. Because of the first stop 33, the hollow needle 9 can only be moved from the resting position to the first puncture position but not further. The first stop is provided by the bearing block 3, which stops the movement of the slider 7 in the first moving direction 35 when it reaches the first puncture position. Further, the dermal access device 1 is provided with a second stop 37, which is differing from the first stop 33 and is implemented as a second mechanical stop for limiting the second moving direction 39 of the slider 7 at a second puncture position of the hollow needle 9. The second moving direction 39 is the direction towards which the slider 7 needs to be moved in order to bring the hollow needle 9 from the first puncture position into the second puncture position.

Figure 5:
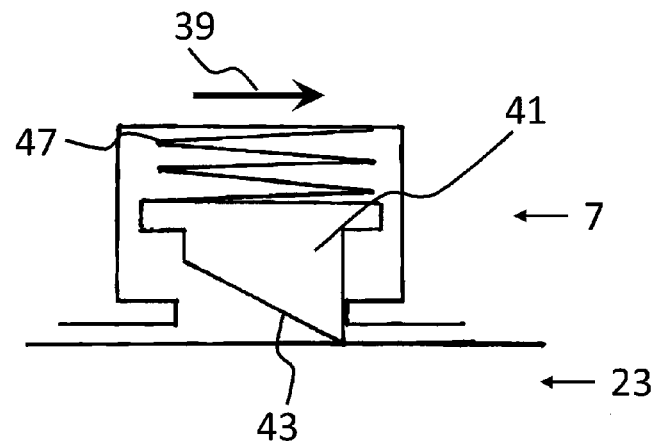
FIG. 5 a section of slider and guiding shaft.
Figure 6:
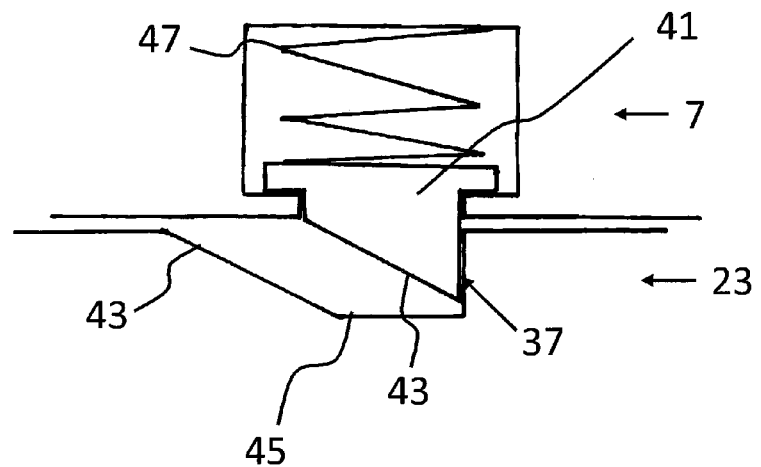
FIG. 6 a section of slider and guiding shaft in the second puncture position of the slider.

In FIGS. 5 and 6 the mechanism by which the second stop 37 is implemented is sketched. Here, the slider 7 is provided with a lock element 41 that has a sloping face 43 at one of the loose bearings 25. The guiding shaft 23 is further provided by a lock groove 45 with also a sloping face 43 which is corresponding to the lock element 41. When the slider is moved from the first puncture position towards the second moving direction 39, with reaching the second puncture position, the lock element 41 is pressed into the lock groove 45 via a spring 47, whereby the movement of the slider 7 is limited in the second moving direction. This is shown in FIG. 6, wherein in FIG. 6 a position of the slider 7 is pictured, where the hollow needle 9 is positioned in the second puncture position. Because of the sloping face 43 of the lock element 41 and the lock groove 45, the movement of the slider 7 towards the first moving direction is not limited by the lock groove and lock spring.

The dermal access device 1 is further provided by a spring used as a readjusting device 49, by which the hollow needle 9 can be brought from the first to the second puncture position. As a result of the readjusting device, which is arranged at the bearing block 3 and is acting on the slider 7, the slider 7 is automatically brought to the second puncture position, meaning without further interaction of the user. Thus, the user does not need to pull back the slider 7 after reaching the first stop.

At the bearing block 3, an inspection device 51 implemented as a lens with cross lines, is arranged for viewing the puncture position of the hollow needle 9 into the skin 5. Because the inspection device 51 is implemented as a lens, it is possible to align the dermal access device 1 according to the structures on the skin surface 15, so that the puncture position of the hollow needle can be chosen in the optimum. The puncture position can also be observed during the injection procedure by using the inspection device.

In order to combine the hollow needle 9, which is partly situated inside of the slider 7 and shows a bent profile 53, with a fluid reservoir 55, a connection device 57 implemented as a flat area is arranged at the slider 7. The connection device 57 is arranged at that side of the slider 7 which is facing away from the skin surface 15. With the help of the connection device 57, a connection between the hollow needle 7 and the fluid reservoir 55 to be attached to will provided. In order to filter possible contamination out of the fluid to be injected, a filter 59 is arranged at the connection device.

Figure 7:
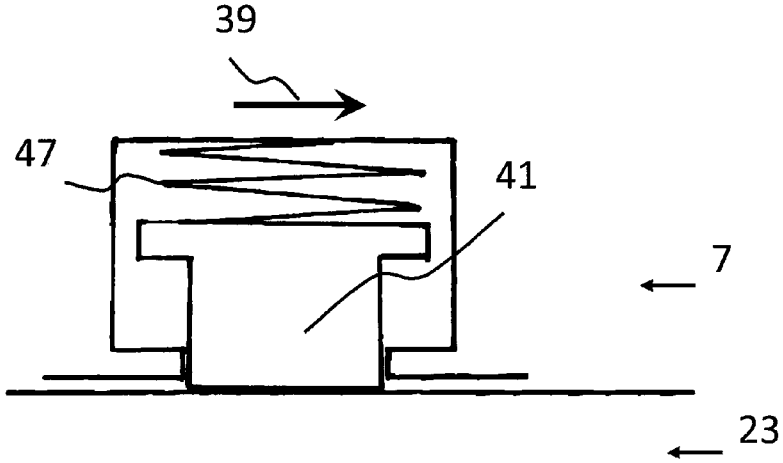
FIG. 7 a section of slider and guiding shaft.
Figure 8:
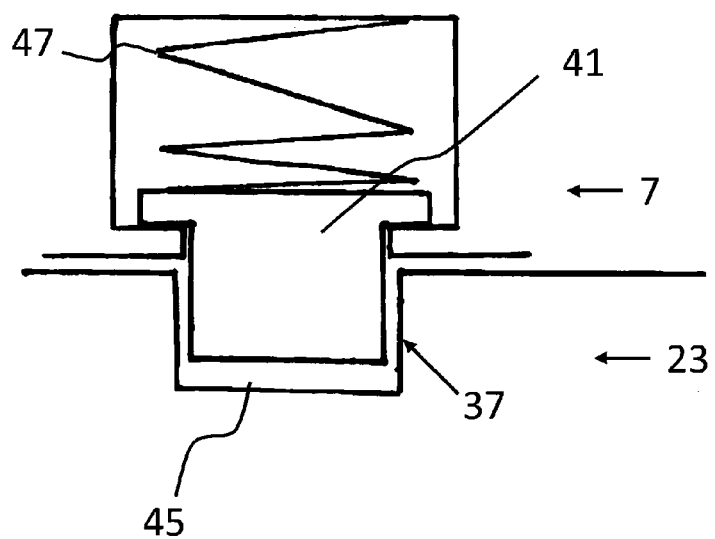
FIG. 8 a section of slider and guiding shaft in the second puncture position of the slider; and finally FIG. 9 a dermal access device with a fluid reservoir in a sectional view.

In a second exemplary embodiment, shown in FIGS. 7 and 8, that otherwise does not differ from the first exemplary embodiment, the slider 7 is detachably fixed at the bearing block 3 in the second puncture position of the hollow needle 9. Here, the lock element 41 as well as the lock groove is provided with a square shaped cross section, so that when reaching the second puncture position of the hollow needle 9, the slider 7 is neither movable towards the first 35 nor towards the second moving position 39. This is shown in FIG. 8. In order to detach the fixation a not shown detachment mechanism is provided. A retaining mechanism is arranged at the slider 7, in order to prevent an unwanted fixation of the slider 7 at the bearing block 3 during a movement in the first moving direction 35 from the resting position to the first injection position. With the help of the retaining mechanism it is avoided, that the lock element 41 is pressed into the lock groove 45. As soon as the first puncture position is reached, the retaining mechanism is deactivated, so that the slider 7 can be fixed at the bearing block 3 via the lock element 41 and the lock groove 45 during the movement in the second moving direction 39. The retaining mechanism as well as the detachment mechanism is not shown in the Figures for reasons of visualisation.

In a third exemplary embodiment, shown in FIG. 9, which otherwise does not differ from the first and second exemplary embodiment, the dermal access device 1 is provided by a fluid reservoir 55 for storing a liquid to be injected. The fluid reservoir 55 is implemented as a bag and inseparably connected to the slider 7.

The disclosed features as described in the above description, claims and Figures can be of importance for the realisation of the invention in its different embodiments in any combination as well as individually.

REFERENCE NUMBERS

1
3 bearing block
5 skin
7 slider
9 hollow needle
11 needle tip
13 sharpened cut
15 skin surface
17 puncture angle 19 fixation device
21 guidance device
23 guidance shaft
25 loose bearing
27 needle guidance device
29 first distance
31 second distance
33 first stop
35 first moving direction
37 second stop
39 second moving direction
41 lock-element
43 sloping face
45 lock groove
47 spring
49 readjusting device
51 inspection device
53 bent profile
55 fluid reservoir
57 connection device
59 filter

The invention claimed is:

1. A dermal access device for fluid injection comprising:
a bearing block for fixation of the dermal access device onto the skin of a patient;
a movable slider connected to the bearing block; and
a hollow needle arranged at the slider for puncturing the skin, the needle comprising a needle tip,
wherein the dermal access device comprises a first stop for limiting a first moving direction of the slider at a first puncture position of the hollow needle,
wherein the dermal access device comprises a second stop at a second puncture position of the hollow needle, differing from the first stop, for limiting a second moving direction of the slider,
wherein the slider is moveable in the second moving direction from the first stop at the first puncture position to the second stop at the second puncture position such that the needle tip in the first puncture position has a greater distance to the bearing block than in the second puncture position, and
wherein the hollow needle is exposed at the first puncture position and at the second puncture position.

2. A dermal access device according to claim 1, wherein the hollow needle creates a puncture angle with respect to the skin surface when puncturing the skin, the puncture angle not exceeding 25°.

3. A dermal access device according to claim 1, wherein the position of the slider is fixable relatively to the bearing block at the second puncture position of the hollow needle.

4. A dermal access device according to claim 1, wherein the dermal access device comprises a readjusting device, by which the hollow needle can be repositioned from the first to the second puncture position.

5. A dermal access device according to claim 1, wherein the dermal access device comprises a guidance device for the movable connection of the slider and the bearing block.

6. A dermal access device according to claim 1, wherein the hollow needle can be positioned in a resting position, and wherein the hollow needle is arranged within a corresponding needle guidance device for the hollow needle of the bearing block in the resting position.

7. A dermal access device according to claim 1, wherein the dermal access device comprises a fixation device for fixing the bearing block onto the skin surface.

8. A dermal access device according to claim 1, wherein the bearing block comprises an inspection device for viewing the puncture position of the hollow needle.

9. A dermal access device according to claim 1, wherein the dermal access device comprises a fluid reservoir for the storage of a fluid that will be injected.

10. A dermal access device according to claim 1, wherein the slider comprises a connection device for combining the hollow needle with a fluid reservoir.

11. A dermal access device according to claim 10, wherein the connection device comprises a filter.

* * * * *